(12) United States Patent
Bergfjord

(10) Patent No.: US 10,583,311 B2
(45) Date of Patent: Mar. 10, 2020

(54) COLLIMATION APPARATUS FOR RADIOTHERAPY

(71) Applicant: Elekta AB (Publ), Stockholm (SE)

(72) Inventor: Per Harald Bergfjord, West Sussex (GB)

(73) Assignee: ELEKTA AB (PUBL), Stockholm (SE)

( * ) Notice: Subject to any disclaimer, the term of this patent is extended or adjusted under 35 U.S.C. 154(b) by 520 days.

(21) Appl. No.: 15/309,611

(22) PCT Filed: May 13, 2015

(86) PCT No.: PCT/EP2015/060646
§ 371 (c)(1),
(2) Date: Nov. 8, 2016

(87) PCT Pub. No.: WO2015/173327
PCT Pub. Date: Nov. 19, 2015

(65) Prior Publication Data
US 2017/0143995 A1 May 25, 2017

(30) Foreign Application Priority Data

May 13, 2014 (GB) .................................. 1408470.1
Jan. 23, 2015 (GB) .................................. 1501165.3

(51) Int. Cl.
*A61N 5/10* (2006.01)
*G21K 1/04* (2006.01)
*G21K 1/02* (2006.01)

(52) U.S. Cl.
CPC ........... *A61N 5/1045* (2013.01); *G21K 1/025* (2013.01); *G21K 1/046* (2013.01); *A61N 2005/1095* (2013.01)

(58) Field of Classification Search
CPC .... A61N 2005/1089; A61N 2005/1095; A61N 5/1045; G21K 1/025; G21K 1/046
See application file for complete search history.

(56) References Cited

U.S. PATENT DOCUMENTS 4,672,212 A * 6/1987 Brahme ............... A61N 5/1045
250/505.1
2010/0166150 A1* 7/2010 Perkins ............... A61N 5/1042
378/148

(Continued)

FOREIGN PATENT DOCUMENTS

WO WO 2008/141667 A1 11/2008
WO WO 2013/180883 A1 12/2013

OTHER PUBLICATIONS

International Search Report and Written Opinion in International Application PCT/EP2015/060646, dated Jul. 28, 2015.

(Continued)

*Primary Examiner* — Chih-Cheng Kao
(74) *Attorney, Agent, or Firm* — Finnegan, Henderson, Farabow, Garrett & Dunner LLP

(57) ABSTRACT

Embodiments disclose a radiotherapy apparatus comprising a source of radiation configured to emit a beam of radiation and a collimator structure configured to limit a lateral extent of the beam, the collimator structure including a primary collimator configured to shape the beam, a first collimator comprising a plurality of adjacent elongate leaves, the leaves being extendable into the beam in a first direction transverse to the beam, and a block collimator including an aperture configured to permit the beam to pass through, the block collimator being extendable into the beam in a second direction transverse to the beam and transverse to the first direction. In some embodiments, the aperture may be cone-shaped or a through-hole, which may be empty or filled with a radiotransparent material. In some embodiments, the block collimator may include a plurality of apertures, which may be of varying dimensions.

20 Claims, 6 Drawing Sheets

(56) References Cited

U.S. PATENT DOCUMENTS

2013/0221243 A1* 8/2013 Perkins ................ A61N 5/1042
378/65
2014/0112453 A1* 4/2014 Prince .................... G21K 1/046
378/152

OTHER PUBLICATIONS

United Kingdom Search Report in GB Application 1408470.1, dated Dec. 3, 2014.

* cited by examiner

COLLIMATION APPARATUS FOR RADIOTHERAPY

CROSS-REFERENCE TO RELATED APPLICATIONS

This application is a national phase of International Application No. PCT/EP2015/060646, filed on May 13, 2015, which claims priority to GB Application No. 1501165.3, filed on Jan. 23, 2015, and to GB Application No. 1408470.1, filed on May 13, 2014. The contents of the above-referenced applications are expressly incorporated herein by reference in their entireties.

FIELD OF THE INVENTION

The present invention relates to collimation apparatus for use in radiotherapy.

BACKGROUND ART

Radiotherapy consists of the application of harmful radiation to lesions (such as tumours) within the body. The radiation interferes with cellular processes within the lesion and alleviates the condition. A principal concern within radiotherapy is to maximise the dose that is delivered to the lesion and minimise the effect of dose that is delivered to surrounding healthy tissue. This is done in a number of ways.

One is to deliver the dose in a number of "fractions", separated over time such as on sequential days. Another is to deliver the radiation from multiple different directions, thus delivering only a partial dose to the surrounding tissue. Often, this is done by mounting the radiation source on a gantry that is rotatable around an axis and directed along a beam direction that co-incides with that axis, thus delivering radiation from (potentially) all directions within a plane transverse to the axis. Another method is to shape the cross-sectional profile of the beam using suitable collimators, such as to conform to the external cross-section of the lesion when viewed along the beam axis, or to another shape calculated to deliver a dose that will build up towards a desired three-dimensional dose distribution. Usually, some combination of all three will be employed.

In relation to the collimation of the beam, most tumours can be dealt with using a combination of block collimators and a so-called "multi-leaf" collimator. A block collimator is a solid block of radiopaque material such as tungsten, which usually has a straight front edge that spans the entire width of the device's aperture, and which can be advanced and/or withdrawn across the aperture in a direction transverse to the front edge. Thus, the block collimator has the effect of adjusting the width of the aperture as needed. A pair of such collimators arranged face-to-face can thus narrow the aperture from both opposing sides.

A multi-leaf collimator such as the one disclosed in our earlier application EP-A-0,314,214 comprises an array of long, narrow, deep leaves of radiopaque material that can each be extended into and out of the aperture. Arranged side-by-side, the tips of the leaves therefore define a chosen shape which can be varied at will by extending or retracting individual leaves.

Both the leaves and the block collimators usually have rounded tips in order to reduce the penumbra that they cast and thus improve the definition of the beam that is allowed through. This does therefore mean that opposing collimator elements cannot be extended so that they meet and close the field completely. Usually, an aperture will be collimated by a pair of opposed block collimators operating in one direction (say, the y direction) and a pair of opposed multi-leaf collimator ("MLC") banks operating in the transverse direction (say, the x direction), both directions being transverse to that of the beam (the z direction). Our earlier application WO2008/141667 discloses a design for the block collimator leaves which can co-operate with the MLC leaves so as to minimise the necessary weight of the block collimator elements; the reader is specifically directed to that disclosure (which is incorporated herein by reference) for a fuller understanding of the present invention.

To produce very small radiation fields, the resolution of a standard MLC and block collimator is usually too coarse, and the rounded tips of both are unsuited to forming very narrow beams. Therefore, one of a micro-MLC or "stereotactic cones" are often used. A micro-MLC is akin to a standard MLC but much smaller. This is however very difficult to engineer, as the leaves are very thin and therefore less rigid. Stereotactic cones offer a range of preset shapes and sizes, such as 5 mm, 10 mm, 15 mm and 20 mm diameter circles, and are provided as "add-on" collimators that can be attached to the radiation head as and when needed. These are usually fitted to the exterior of the radiation head, in the path of the beam, so as to place them as close as possible to the patient for best accuracy. As an alternative, US2014/0048727 discloses stereotactic cones that are integrated into the beam generation system adjacent the primary collimator; this will be more convenient for the operators but at the expense of lesser accuracy in delivery.

SUMMARY OF THE INVENTION

We would like to provide stereotactic cones that can be placed into the beam easily and securely, but can nevertheless be in the correct position to achieve the necessary levels of accuracy, i.e. close to the patient.

To that end, the present invention proposes a radiotherapy apparatus comprising a source of radiation adapted to emit a beam of radiation, and a collimator structure for limiting the lateral extent of the beam, the collimator structure comprising a primary collimator, a collimator comprising a plurality of adjacent elongate leaves, each being controllably extendable into the beam in a first direction transverse to the radiation beam, and at least one block collimator, controllably extendable into the beam in a second direction transverse to the radiation beam and transverse to the first direction, wherein the block collimator has at least one aperture aligned to permit the beam to pass through.

Thus, when a stereotactic cone is needed, the block collimator can be extended sufficiently to place the aperture within the radiation beam, the aperture then acting as a stereotactic cone. The aperture is thus preferably cone-shaped. When a stereotactic cone is not needed, the block collimator can be used as normal and the MLC leaves extended as necessary in order to cover the aperture. As the block collimator can be located beneath the MLC/first collimator, it can be substantially closer to the patient than that of US2014/0048727. Indeed, it is possible for the block collimator to be the last beam-shaping element of the radiation head, and therefore very close to the patient indeed. Thus, the block collimator may be adjacent (in the beam direction) to an external cover of the source of radiation.

The aperture can be a through-hole, which may be empty or filled with a radiotransparent material. There can be several apertures in the block collimator, in order to provide several stereotactic cones. These may be of varying dimensions. Where there are at least three apertures, the minimum total spacing on each side of an aperture is preferably 2d, such that 2d≥(w−a) where w is the width of the leaves of the first collimator and a is the diameter of the aperture. If the spacings on either side of the aperture is unequal, then 2d will be the sum of the two spacings and d will be the average of them. Ideally, no two of these apertures are the same size.

The block collimator can have a central region of a first thickness flanked by side regions of a second and lesser thickness, with the aperture being located in the central region. It may have a front edge portion of the first thickness. Alternatively, it may comprise a spine portion extending in the second direction and in which the aperture is located, and a frontal portion extending transversely to the spine portion in either direction to define a T shape. Thus, the frontal portion can extend in the first direction. The spine region can thus be of a first thickness, flanked by side regions of a second and lesser thickness.

Typically, there will be two block collimators, i.e. a first block collimator and a second block collimator, each extending into the beam from opposing sides. In this case, we prefer there to be apertures on both block collimators. Preferably, the first block collimator contains apertures that are all of different sizes to each of the apertures on the second block collimator, to avoid duplication and provide the maximum range of sizes. To allow the greatest number of apertures in the space available, and thus offer the widest choice of sizes, the smallest aperture of one block collimator can be sized between the sizes of the smallest and the second-smallest apertures of the other block collimator. Likewise, the largest aperture of one block collimator can be sized between the sizes of the largest and the second-largest apertures of the other block collimator. We prefer that where a block collimator has more than one aperture, the smallest is located nearest the front edge of the block (i.e. the edge that lies in the radiation beam).

The apparatus preferably includes a control apparatus adapted, when in a first mode, to extend leaves of the first collimator in order to cover the aperture. In a second mode, corresponding to the use of stereotactic cones, it will extend the block collimator so as to place the aperture or one of them in the radiation beam, and cover any other apertures with leaves of the MLC. It may also cover any remaining areas or locally thinner areas of the block collimator with leaves of the MLC.

BRIEF DESCRIPTION OF THE DRAWINGS

An embodiment of the present invention will now be described by way of example, with reference to the accompanying figures in which.

DETAILED DESCRIPTION OF THE EMBODIMENTS

Figure 1:
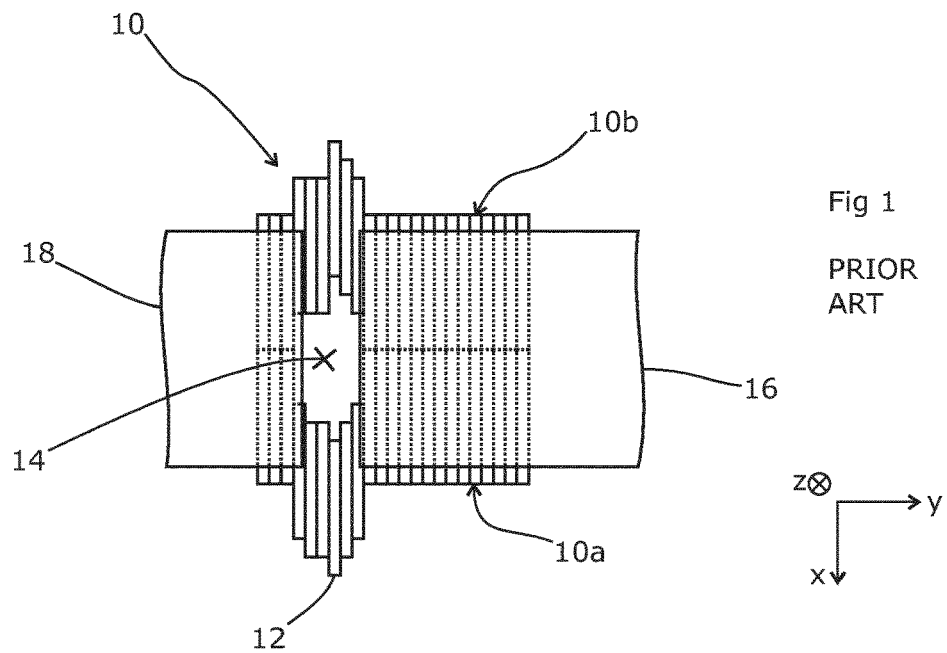
FIG. 1 shows a known arrangement of a block collimator and a multi-leaf collimator.

Referring to FIG. 1, a view along the beam axis of a conventional collimation arrangement is shown. The purpose of the collimators is to allow the transmission of a beam which has a desired cross-section and to provide as complete shielding as possible across the remainder of the beam field (i.e. the maximum extent of the beam). To allow shaping of the beam, a multi-leaf collimator (MLC) 10 is provided which comprises a series of individual leaves 12 of a radiopaque material such as tungsten, arranged side-by-side relative to each other, in two opposing arrays 10a, 10b. Thus, the lower array 10a extends into the beam field in the x direction from one side of the field, and the upper array 10b extends into the beam field in the x direction from the opposing side of the field. The leaves 12 can each be moved independently of the others so as to define a chosen shape 14 between the tips of the opposing leaf banks 10a, 10b. Each leaf is thin in its transverse (y) direction to provide good resolution, is deep in the (z) direction to provide adequate absorption, and long in its longitudinal (x) direction to allow it to extend across the field to a desired position. Generally, the longitudinal length of the leaf will be greater than its depth, and both will be much greater than its transverse thickness.

To allow for the fact that directly opposing MLC leaves 12 from opposing banks 10a, 10b cannot fully approach each other (as described above) to close off parts of the field, and that there is usually some degree of leakage through the gap between adjacent leaves, a pair of block collimators 16, 18 are also provided. These consist of a pair of solid blocks of radiopaque material such as tungsten, which extend inwards in the y direction from the two opposing sides of the field. They have a front edge that spans the entire width of the field and which is straight (in the x-direction), and which can each be advanced and/or withdrawn independently across the field in a direction transverse to the front edge. Thus, the block collimators provide additional shielding in locations spaced from the field shape along the y direction, limiting inter-leaf leakage between the tips of opposing leaves and between adjacent leaves.

Figure 2:
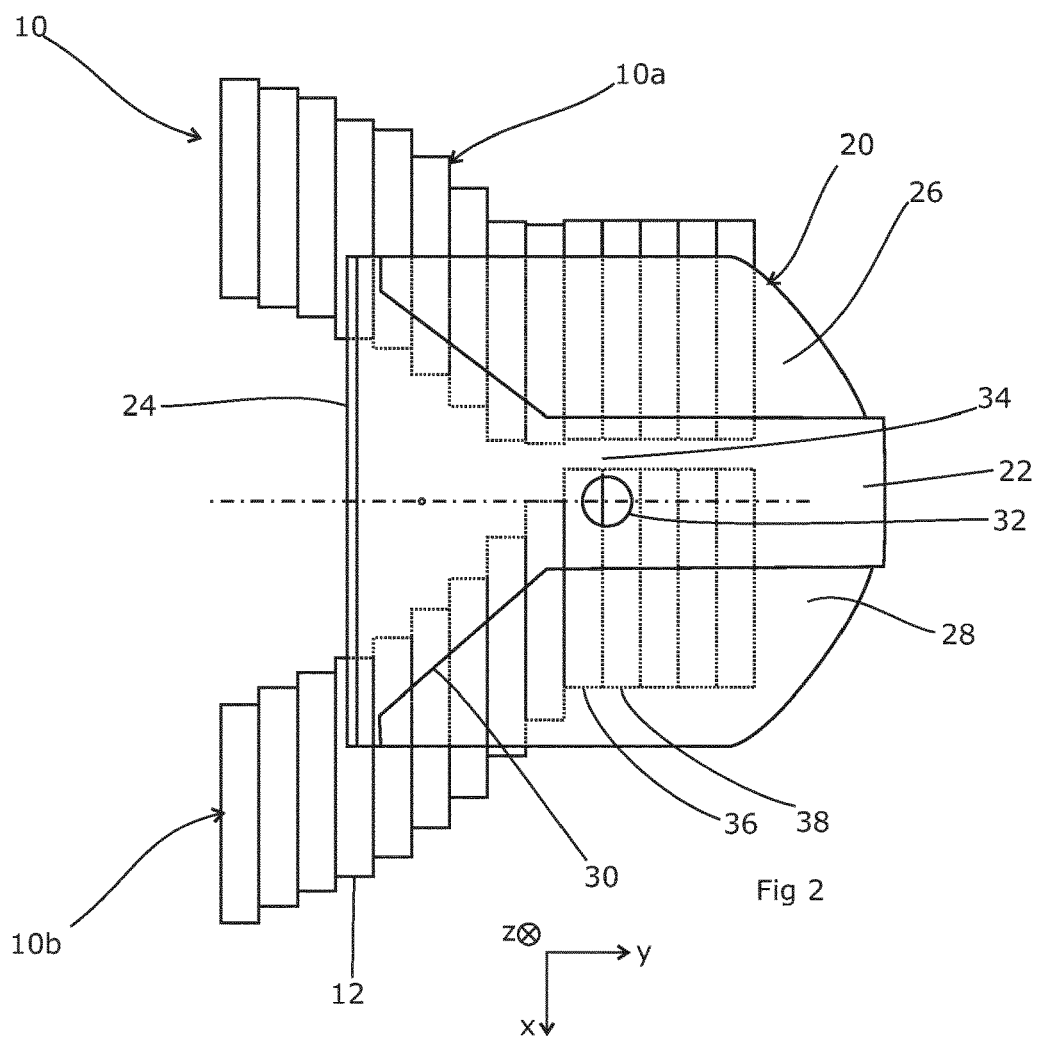
FIG. 2 shows a block collimator and a multi-leaf collimator for a radiotherapy head, according to the present invention, viewed along the beam axis.

FIG. 2 shows a development of this arrangement, based on the concept of our earlier disclosure WO2008/141667 but incorporating the present invention as well. As disclosed in WO2008/141667, the block collimator 20 is reduced in weight by having a spine 22 and a front edge 24 that are of the usual thickness, flanked on either side of the spine 22 and behind the front edge 24 by lateral regions 26, 28 that are substantially thinner in the (z) direction of the beam. FIG. 2 shows one block collimator 20 but there will usually be a second block collimator extending from the opposite side of the field. As shown in FIG. 2 and WO2008/141667, the MLC leaves 12 in the region covered by the block collimator 20 are extended so as to cover the thinner lateral regions 26, 28. The inevitable gap between opposing leaves 12 is therefore covered by the thicker spine region 22, whereas the lateral regions 26, 28 only need to block leakage from between the MLC leaves 12. A triangular transition region 30 is provided at the junction of the spine 22 and the front edge 24 which is of substantially the same thickness of the spine 22, in order to allow time for the MLC leaves 12 to extend or retract in the x direction to the spine position, while the block collimator 20 is itself extending or retracting across the field in the y direction. The minimum shape and dimensions of the transition region 30 are dictated by the various movement speeds of the collimator elements as explained in WO2008/141667.

The specific shapes of the spine 22 and the transition region 30 can be varied as desired and (in particular) it is not necessary for the spine 22 to be at the centreline of the block collimator, although that may often be the most convenient location. Equally, it is not necessary for the block collimator of the present invention to be of the type described in WO2008/141667 (although we do prefer this), and the invention can be applied to simple plain block collimators such as that shown in FIG. 1 or other designs of block collimator.

According to the present invention, a radiotransparent aperture 32 is provided in the block collimator. Normally, this would be avoided at all costs, as the purpose of the block collimator is to provide a complete block to radiation and an aperture goes against this principle. However, it means that when desired, the block collimator can be extended so as to locate the aperture 32 at a desired position in the beam field, usually the centre. This implies that the aperture should ideally be at the centreline of the block collimator. Where the block collimator has a spine 22, the aperture 32 is preferably located on the spine 22 in order to provide adequate attenuation in the regions immediately around the aperture 32. The spine may be thicker in this region, if desired. The MLC leaves 12 can then be extended to cover the lateral regions 26, 28 as before.

The aperture 32 can thus act as a stereotactic cone, limiting the radiation beam to just a pencil beam of the desired diameter (dictated by the size of the aperture). The aperture 32 is therefore preferably frusto-conical in shape, matching the divergence angle of the beam at that location so as to provide a beam with the minimum penumbra. The aperture 32 can be hollow, or it can be filled with a radiotransparent material such as perspex or glass.

Where the apparatus is being used in a conventional manner, i.e. collimated by the block collimators and the MLC rather than in a stereotactic manner, the MLC leaves 12 can simply be extended across the aperture 32 in order to cover it and substantially prevent transmission through the aperture 32, as shown in FIG. 2 where individual leaves 36, 38 together cover the aperture 32. The spine 22 may need to be made slightly wider than would otherwise be the case, or offset slightly, to provide an adequate width to cover the gap 34 between opposing MLC leaves 12.

Figure 3:
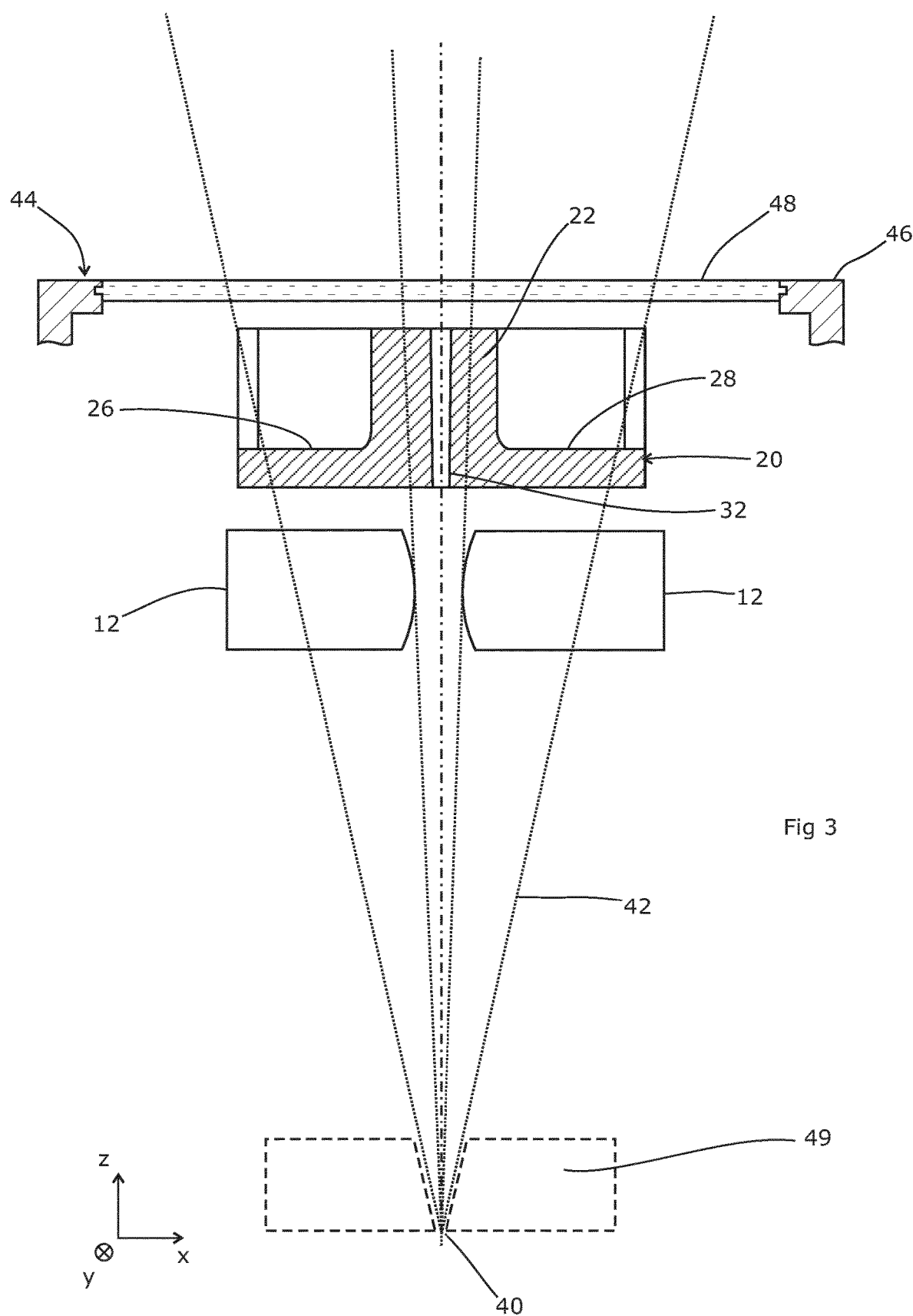
FIG. 3 shows the block collimator and a multi-leaf collimator of FIG. 2, viewed transverse to the beam axis.
Figure 4:
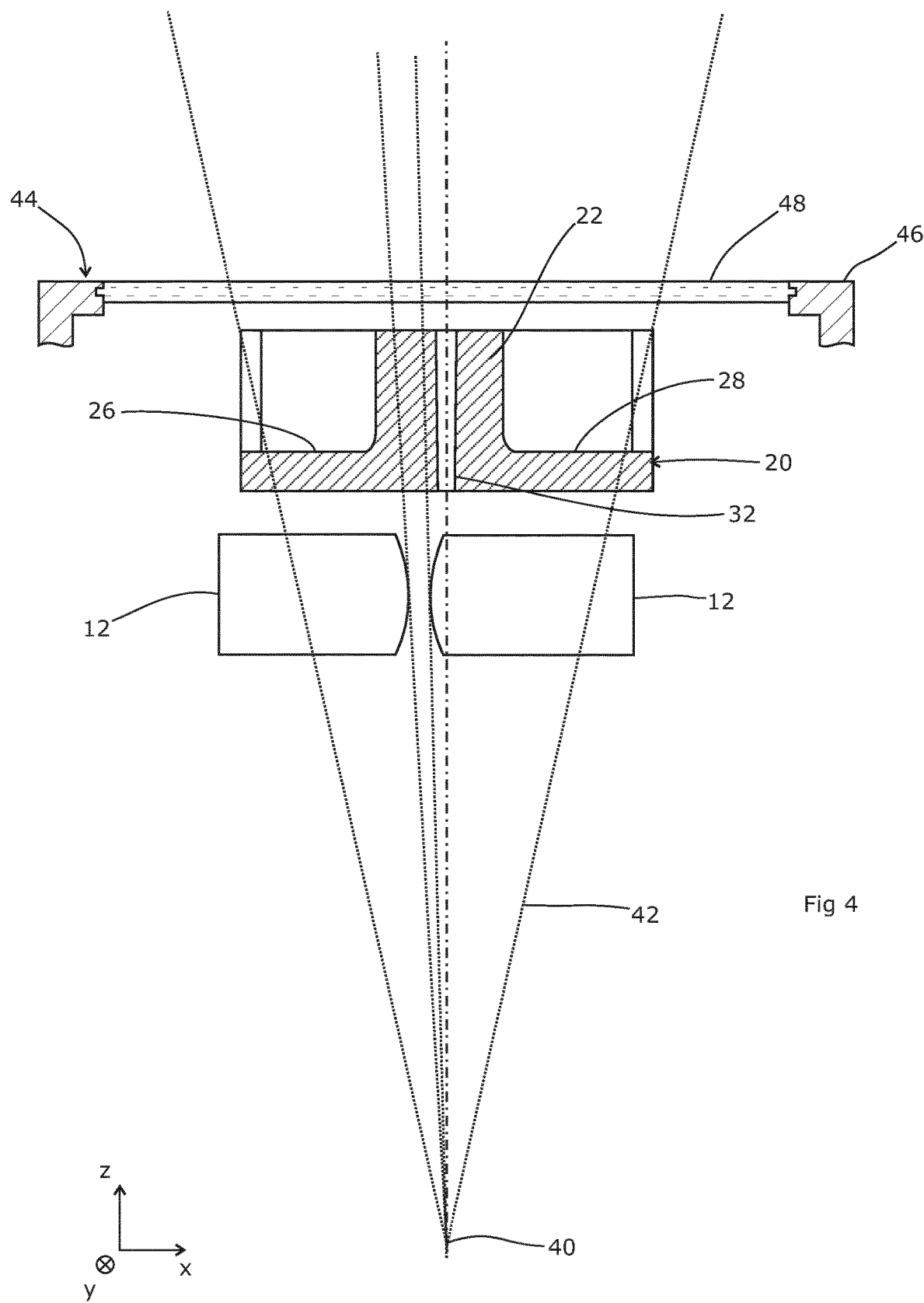
FIG. 4 shows the collimators of FIG. 3, with the stereotactic cone out of use.

FIGS. 3 and 4 shows a cross-section through the relevant parts of the radiotherapy head in the x-z plane of FIG. 2. A conventional pointlike radiation source 40 is formed by an x-ray target (not illustrated in FIGS. 3 and 4) onto which is directed a beam of electrons produced by a linear accelerator (not illustrated in FIGS. 3 and 4). This is shaped by a conical primary collimator 49 which allows a conical x-ray beam 42 to be produced. This is then filtered and measured in the conventional manner. The primary collimator 49 (shown only in FIG. 3) is in the form of a block of a material which is substantially opaque to radiation, such as tungsten, with an aperture (usually frustoconical) machined into it so as to define the extent of the beam of x-rays after they are created at the X-ray target (not shown).

FIG. 3 shows the apparatus in use in a stereotactic cone mode. Thus, the block collimator 20 is positioned so that the aperture 32 is at the centre of the beam field and the block collimator covers substantially all of the beam 42. The MLC leaves 12 are advanced into the beam 42 to cover the thinner lateral regions 26, 28; if the block collimator is a conventional block collimator as illustrated in FIG. 1 then this may be considered unnecessary, although doing so will assist in reducing leakage. The MLC leaves 12 and the block collimators 20 provide the accurate shaping of the beam for radiotherapy. Although the MLC leaves 12 are shown in FIGS. 3 and 4 as being closer to the radiation source than the block collimator 20, those skilled in the art will appreciate that these positions may be reversed, so that the block collimator 20 is closer to the source 40 than the MLC leaves 12.

FIG. 4 shows the apparatus in a normal mode of operation, in which the conical beam formed by the primary collimator (not shown) is shaped by the MLC 10 and the block collimators 20. The illustrated block collimator 20 may be at any position called for by the currently-required beam shape, and the relevant MLC leaves 12 are advanced so as to block the beam 42 over the aperture 32. The opposing leaf 12 will be advanced so as to cover the relevant lateral region 26. The gap between the opposing leaves is covered by a section of the spine region 22 of the block collimator 20 that is adjacent the aperture 32.

FIGS. 3 and 4 also show a part of the housing 44 of the radiotherapy head containing the collimators (etc.). This has an opaque outer section 46 which holds a glass or perspex window 48 through which the collimated beam is emitted. The window may be opaque (so long as it is radiotransparent) but is preferably transparent as radiotherapy heads often include visible light sources that are in optically equivalent positions to the x-ray source, to provide a visual check on the operation of the collimators. As can be seen in FIGS. 3 and 4, the block collimator 20 is the last beam-shaping element of the radiation head, located immediately prior to the window 48 which defines the exterior shape of the head. Thus, the aperture 32 will define as accurate as possible a shape for the stereotactic beam without requiring additional beam-shaping devices to be affixed to the outside of the radiation aperture.

Figure 5:
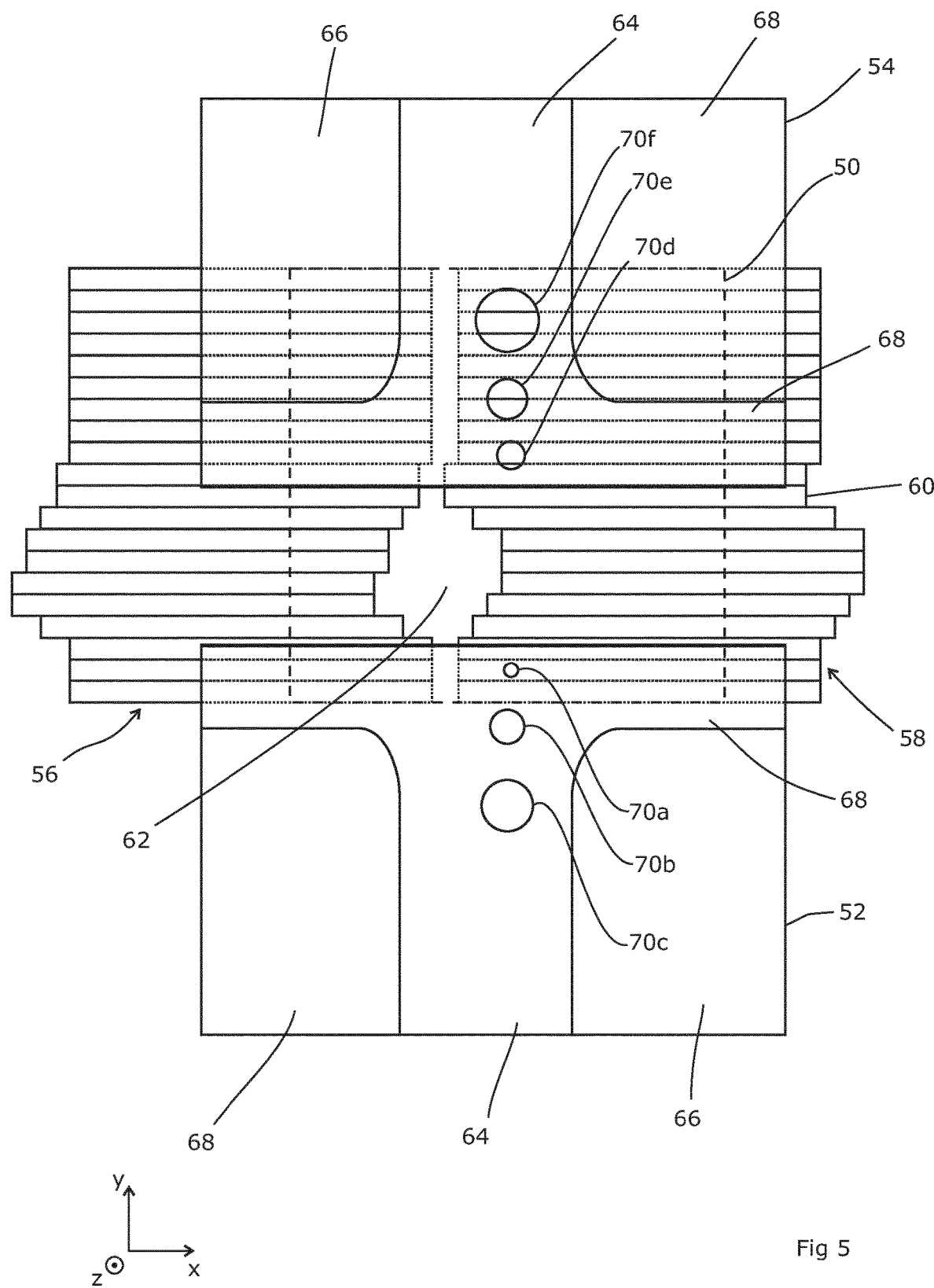
FIG. 5 shows a block collimator and a multi-leaf collimator being a second embodiment of the present invention, with the stereotactic cones being out of use.
Figure 6:
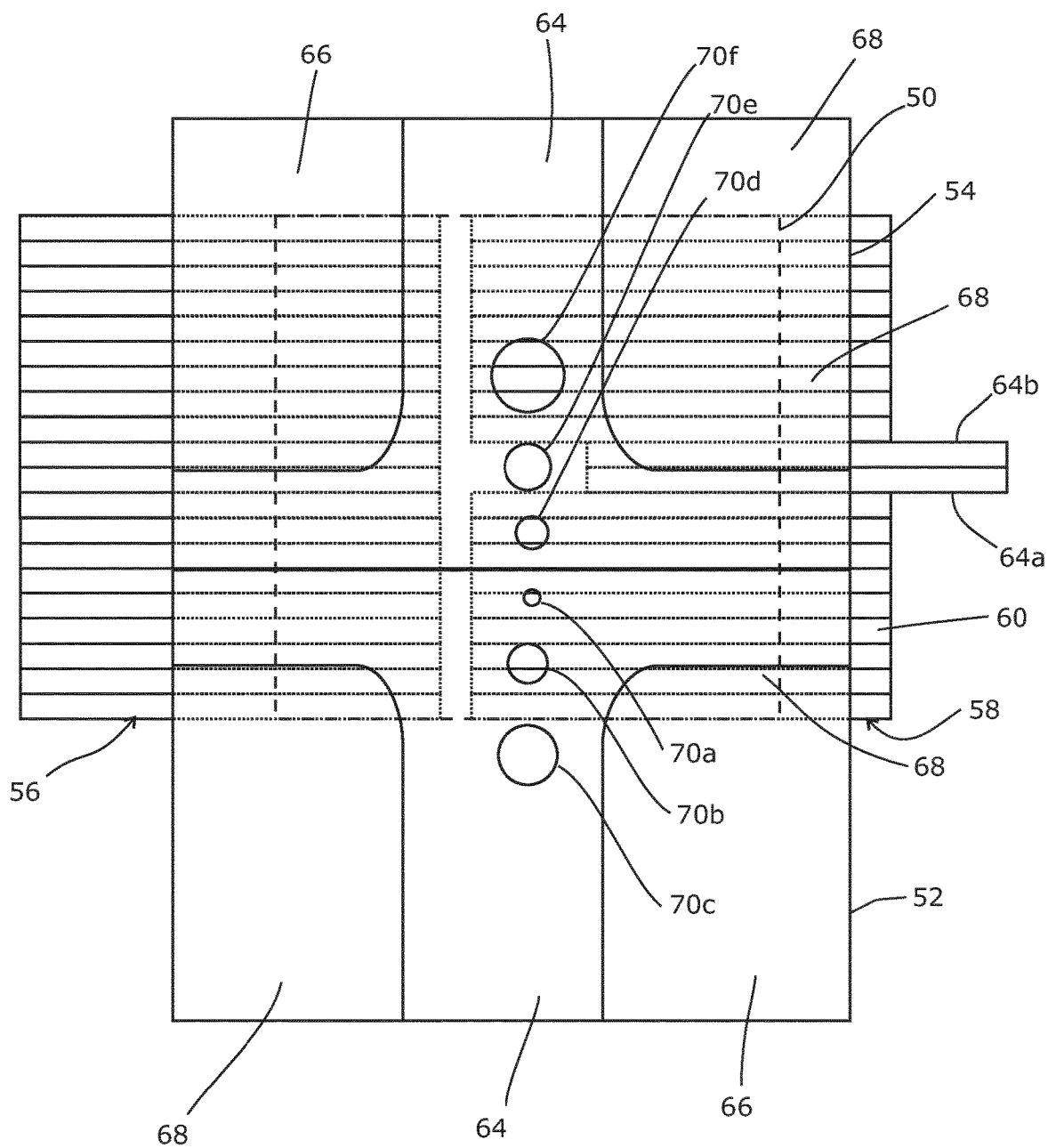
FIG. 6 shows the embodiment of FIG. 5, with a selected stereotactic cone in use.

FIGS. 5 and 6 show a second embodiment of the present invention and illustrate the block collimators and the MLC leaves along the direction of the beam, i.e. the z direction. These collimators are fitted within a radiation head that is otherwise conventional. The radiation head produces an x-ray beam with a rectangular maximum field 50. This is collimated in the y direction, as before, by a pair of block collimators being a first block collimator 52 which extends upwardly (in FIGS. 5 and 6) from the lower part of the field 50 and a second block collimator 54 which extends downwardly from the upper part of the field 50, together delimiting the beam in the y direction. In the x direction, a pair of MLC leaf banks 56, 58 each comprise a plurality of leaves 60 arranged side-by-side and extendable into the field 50 in the x-direction to define a chosen profile. The two collimator sets thus define a desired beam shape 62, with the shape defined by the MLC leaves and the block collimators providing additional backup on either side of the shape.

As before, the block collimators each comprise thinner lateral regions 66, 68 on either side of a central spine region 64 which leads from the rear of the collimator to a front edge 68 of substantially the same thickness as the spine 64. Thus, as before, the MLC leaves 60 are advanced so as to cover the thinner lateral regions 66, 68, with the gap between opposing leaves 60 being covered by the spine region 64.

In this embodiment, each block collimator carries several apertures within its spine region 64, all being of different sizes. Thus, the first block collimator 52 has three apertures 70a, 70b, 70c and the second block collimator 54 has three apertures 70d, 70e, 70f. On each collimator, the apertures 70 are arranged linearly along the respective spine 64, along the centrelines of the blocks 52, 54. The spines 64 are offset slightly from the centre of the blocks 52, 54 so that there is adequate space to one side of the apertures 70 in order to cover the gaps between opposing leaves 60. As illustrated, the spines 64 are straight-sided but this is not necessarily the case and the spines 64 may be narrowed (on one side or the other) in regions away from the apertures 70.

Each aperture 70 is of a different size, in order to offer a choice of sizes for the stereotactic cone. To allow the minimum possible leakage of radiation through the collimator set, the apertures are placed in size order. Thus, the smallest apertures 70 are placed closest to the front edge 68, and the largest apertures 70 are placed furthest from the front edge 68. As the regions of the block collimator 52, 54 closest to the front edge 68 are the parts most commonly in the beam field 50, this minimises the average area of aperture that is in the beam field 50 (and hence covered by an MLC leaf or leaves only) at any particular time.

Likewise, the apertures are distributed between the block collimators 52, 54, so that the smallest aperture 70a is placed on (say) the first block collimator 52, and the second-smallest aperture 70d is placed on the other block collimator 54. The third-smallest aperture 70b is then adjacent the smallest aperture 70a on the first block collimator 52, and so on with the apertures alternating from one block collimator to the other in increasing order of size, allowing the leakage to be minimised.

As the apertures are located along a straight line substantially parallel with the y direction, this means that each successive aperture can be moved (when in use) to a consistent point within the radiation field. This means that the aperture size can be varied effectively independently and without requiring a corresponding adjustment in the head location. In addition, placing that straight line along the centre of the radiation field means that the apertures can be placed at the centre of the field, aligned with the peak in the radiation beam and creating the minimum penumbra. However, other arrangements may allow for a greater number of apertures, if this is felt necessary.

FIG. 6 shows the apparatus in the stereotactic mode. In this instance, the cone size needed is that of the aperture 70e. The first block collimator 52 is therefore withdrawn from the centre of the field and the second block collimator (carrying the selected aperture 70e) is extended to place the aperture 70e at the centre of the radiation field. The MLC leaves 60 are then extended so that their tips lie under the region of the spine 64 adjacent the apertures 70, with the exception of (in this case) two leaves 64a, 64b which are withdrawn as necessary to reveal the selected aperture 70e.

Figure 7:
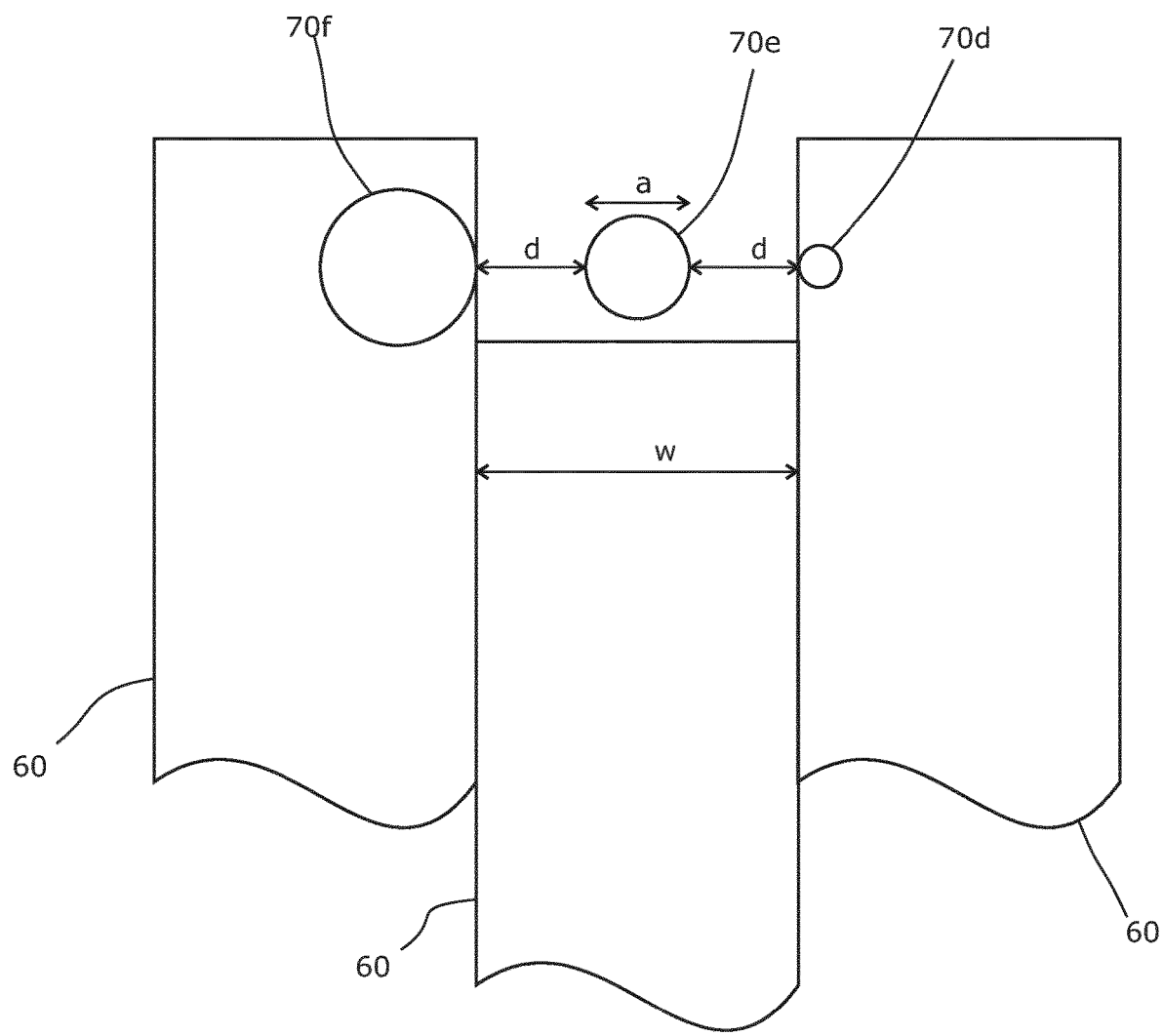
FIG. 7 illustrates the spacing of apertures relative to the leaf size.

In this example, there are three apertures on each block collimator. To ensure that any selected aperture can be revealed exclusively of the others, the spacing between the central aperture 70e and the apertures 70d, 70f on either side should be sufficient to allow the two outer apertures 70d, 70f to be blocked. This calls for the leaves immediately adjacent to the leaf or leaves that are withdrawn to reveal the central aperture 70c, to be capable of completely covering the two outer apertures 70d, 70f. In other words, the spacing between apertures should be sufficient that the leaf or leaves that need to be withdrawn in order to expose the aperture in question should not also expose an adjacent aperture. FIG. 7 illustrates this constraint in practice, in a case where the leaves are wide relative to the aperture sizes, and implies that the aperture spacing is at least d, such that $2d \geq (w-a)$ where w is the width of the leaves 60 of the MLC and a is the diameter of the aperture 70e in question. This is derivable from the inequality $w \leq 2d+a$ which is the constraint that ensures that the particular leaf 60 that is withdrawn in order to reveal the middle aperture 70e does not also expose any part of the adjacent apertures 70d, 70f. If the spacings on either side of the aperture are unequal, then d can be measured as the average of them, i.e. $2d$ will be the sum of the two spacings on either side of the aperture. Where the leaf width is less than the size of the aperture (i.e. $w<a$), other constraints will apply. In general, the exact constraint that applies will depend on the geometry of the system in question, including such factors as the precise intended location of the aperture in use relative to the leaf edges.

Some form of control apparatus will usually be needed in order to send appropriate control instructions to the collimators and to the beam production apparatus. At its simplest, this will, in a first mode, act to extend leaves of the first collimator as required at any one time in order to cover the aperture. In a second mode, corresponding to the use of stereotactic cones, it will extend the block collimator so as to place the aperture or one of them in the radiation beam, and cover any other apertures with leaves of the MLC. It may also cover any remaining areas or locally thinner areas of the block collimator with leaves of the MLC. Usually, such a control apparatus will be a suitably-programmed computer.

It will of course be understood that many variations may be made to the above-described embodiment without departing from the scope of the present invention.

The invention claimed is:

1. A radiotherapy apparatus comprising:
   a source of radiation configured to emit a beam of radiation; and
   a collimator structure configured to limit a lateral extent of the beam, the collimator structure comprising:
      a primary collimator positioned adjacent to the radiation source, the primary collimator comprising a primary aperture configured to shape the beam;
      a first collimator comprising a plurality of adjacent elongate leaves, the leaves being extendable into the beam in a first direction transverse to the beam; and
      a block collimator positioned away from the radiation source, the block collimator comprising a spine region extending in a second direction and an aperture, located on the spine region, configured to permit the beam to pass through, the block collimator being extendable into the beam in the second direction transverse to the beam and transverse to the first direction.

2. The radiotherapy apparatus according to claim 1, wherein the aperture is cone-shaped.

3. The radiotherapy apparatus according to claim 1, wherein the aperture is a through-hole.

4. The radiotherapy apparatus according to claim 1, wherein the aperture is filled with a radiotransparent material.

5. The radiotherapy apparatus according to claim 4, wherein the aperture has a frusto-conical shape configured to limit the beam to a desired diameter.

6. The radiotherapy apparatus according to claim 1, wherein the block collimator includes a plurality of apertures including the aperture and at least one additional aperture.

7. The radiotherapy apparatus according to claim 6, wherein the plurality of apertures have different dimensions.

8. The radiotherapy apparatus according to claim 6, further comprising:
   a control apparatus configured to, in a first mode:

extend the block collimator such that the aperture is placed in the path of the beam; and
extend leaves of the first collimator in order to cover the at least one additional aperture.

9. The radiotherapy apparatus according to claim 1, further comprising:
a control apparatus configured to, in a first mode, extend leaves of the first collimator in order to cover the aperture.

10. The radiotherapy apparatus according to claim 9, wherein the control apparatus is further configured to, in a second mode:
extend the block collimator such that the aperture is placed in the path of the beam.

11. The radiotherapy apparatus according to claim 1, wherein the block collimator further comprises:
a first side region and a second side region flanking the spine region, the first and second side regions having a second thickness that is less than the first thickness.

12. The radiotherapy apparatus according to claim 11, wherein the block collimator further comprises:
a front edge portion having the first thickness.

13. The radiotherapy apparatus according to claim 1, wherein the block collimator further comprises:
a frontal portion extending transversely to the spine region in either direction to define a T shape.

14. The radiotherapy apparatus according to claim 13, wherein the frontal portion extends in the first direction.

15. The radiotherapy apparatus according to claim 13, wherein the spine region is of a first thickness and the block collimator further comprises:
a first side region and a second side region flanking the spine region, the first and second side regions having a second thickness that is less than the first thickness.

16. A collimator structure for a radiotherapy apparatus, the collimator structure comprising:
a primary collimator comprising a primary aperture configured to shape a beam of radiation emitted from a source of radiation, the primary collimator being positioned adjacent to the radiation source;
a first collimator comprising a plurality of adjacent elongate leaves, the leaves being extendable into the beam in a first direction transverse to the beam; and
a block collimator positioned away from the radiation source, the block collimator comprising a spine region extending in a second direction and an aperture, located on the spine region, configured to permit the beam to pass through, the block collimator being extendable into the beam in the second direction transverse to the beam and transverse to the first direction.

17. The collimator structure according to claim 16, wherein the block collimator comprises a plurality of apertures having different dimensions.

18. The collimator structure according to claim 16, wherein the aperture has a frusto-conical shape configured to limit the beam to a desired diameter.

19. The collimator structure according to claim 16, wherein the spine region has a first thickness and the block collimator further comprises:
a first side region and a second side region flanking the spine region, the first and second side regions having a second thickness that is less than the first thickness.

20. The collimator structure according to claim 19, wherein the block collimator further comprises:
a front edge portion having the first thickness.

* * * * *